Figure 1:
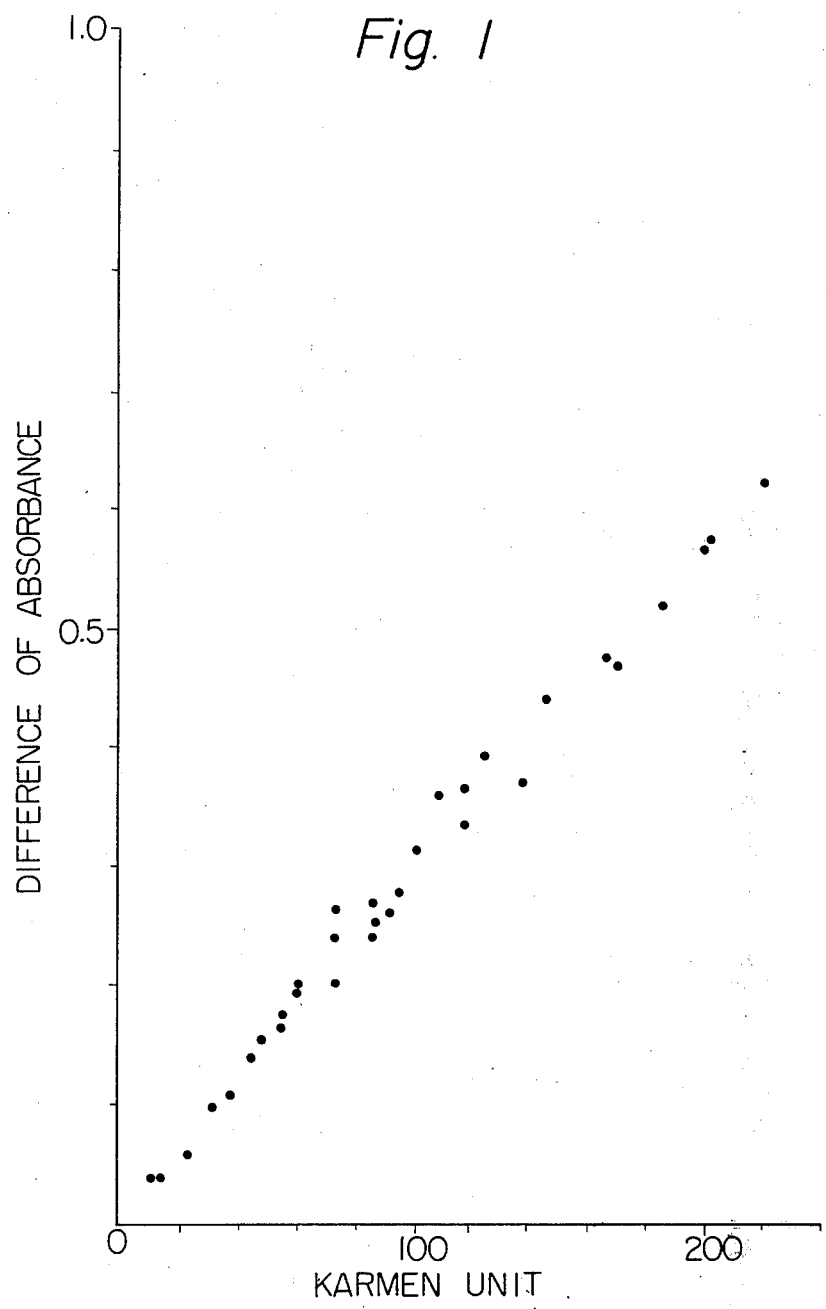

| United States Patent [19] | [11] 4,017,365 |
|---|---|
| Nakayama et al. | [45] Apr. 12, 1977 |

[54] METHOD FOR DETERMINING ENZYME ACTIVITY

[75] Inventors: Toshimasa Nakayama, Kawasaki; Motoshi Kitamura, Tokyo, both of Japan

[73] Assignee: Chugai Seiyaku Kabushiki Kaisha, Tokyo, Japan

[22] Filed: Oct. 7, 1974

[21] Appl. No.: 512,620

[30] Foreign Application Priority Data

Oct. 9, 1973 Japan .............................. 48-112846

[52] U.S. Cl. ........................................ 195/103.5 R
[51] Int. Cl.$^2$ ........................................ G01N 31/14
[58] Field of Search ............ 195/103.5 R; 23/230 B

[56] References Cited

UNITED STATES PATENTS

| 3,816,262 | 6/1974 | Monte et al. | 195/103.5 R |
| 3,838,011 | 9/1974 | Hagen et al. | 195/103.5 R |
| 3,853,465 | 12/1974 | Rush et al. | 23/230 B |

*Primary Examiner*—Lionel M. Shapiro
*Assistant Examiner*—C. A. Fan
*Attorney, Agent, or Firm*—Browdy and Neimark

[57] ABSTRACT

Difficulty in using the Karmen method due to lipemic turbidity and substances absorbing ultraviolet rays in serum can be prevented by reducing the amount of GOT or GPT-containing sample and adding nonion surfactant to the reaction system.

4 Claims, 2 Drawing Figures

METHOD FOR DETERMINING ENZYME ACTIVITY

The present invention relates to the improvement in a method for determining the activity of glutamic acidoxaloacetic acid aminotransferase (hereinafter referred to as "GOT") and glutamic acid-pyruvic acid aminotransferase (hereinafter referred to as "GPT"), that is, a method referred to as the "Karmen method".

The Karmen method comprises coupling GOT or GPT with dehydrogenase which reacts with substrates of GOT or GPT and determining consumption of coenzyme of the hydrogenase, that is, reduced niacin adenine dinucleotide (hereinafter referred to as $NADH_2$) by determining ultraviolet absorbance thereof. The principle of the determination is indicated as follows:

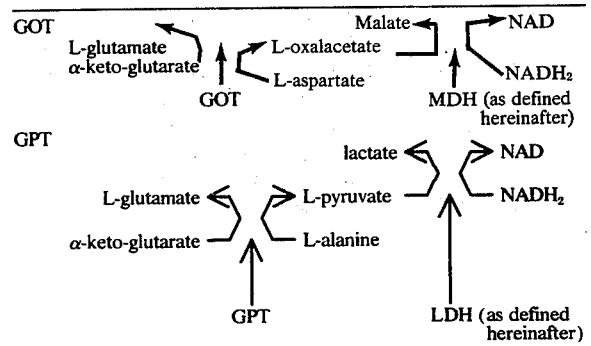

Concretely, in the determination of GOT, α-ketoglutaric acid, L-aspartic acid, malic dehydrogenase (hereinafter referred to as MDH) and $NADH_2$ are added with suitable buffer solution to a sample to be determined and, in the determination of GPT, α-keto-glutaric acid, L-alanine, lactic dehydrogenase (hereinafter referred to as LDH) and $NADH_2$ are added with suitable buffer solution to a sample. After enzyme reactions of these mixtures, the reduction in absorbance at 340 mμ of $NADH_2$ is determined periodically and the reduction speed (initial speed) of absorbance within the time range wherein the absorbance reduces linearly is cultivated.

The Karmen method is the preferred method for determining the activity of GOT and GPT. But in case that serum is used as sample, it is often difficult to determine GOT or GPT activity by the method, since the determination must be conducted at many points while the enzyme reaction proceeds because of hindrance by lipemic turbidity and substances absorbing ultraviolet rays contained in serum and the time range wherein the reduction in absorbance of $NADH_2$ is linear, is narrow.

It is the object of this invention to provide a method for determining GOT and GPT activity by a modified Karmen method whereby the time range wherein the reduction in optical absorbance of $NADH_2$ is linear becomes broad and whereby GOT or GPT activity can be determined by determining ultraviolet absorbance of $NADH_2$ only once.

The method of this invention is characterized by reducing the amount of GOT or GPT-containing sample and adding nonion surfactant to the reaction system in the Karmen method comprising coupling GOT or GPT with dehydrogenase which reacts with substrates of GOT or GPT and determining the reduction in ultraviolet absorbance of $NADH_2$, that is, coenzyme of the dehydrogenase to determine GOT or GPT activity.

According to the Karmen method, 0.2 ml of GOT or GPT containing sample per 3 ml of substrate containing buffer solution is usually used. On the other hand, according to the method of this invention one twentieth to one fifth of this volume — that is, 0.04 – 0.01 ml of sample, is used.

Any nonion surfactant which doesn't inhibit intended enzyme activity and doesn't absorb ultraviolet rays can be used in the method of this invention. For example, polyoxyethylene alkyl esters, polyoxyethylene sorbitan alkyl ester, isooctylphenyl polyethoxyalcohols and polyoxyethylene castor oil are used in this method. Particularly isooctylphenyl polyethoxy alcohol (available from Rohm and Haas Co. under the trade name "Triton X-100") and polyoxyethylene castor oil (available from Nihon Surfactant Kogyo Kabushiki Kaisha under the trade name "Nikkol CO-60TX") are most suitable.

In the determination of GOT or GPT according to the Karmen method, a part of the substrates, that is L-aspartic acid and α-keto-glutaric acid for GOT and L-alanine and α-ketoglutaric acid for GPT are dissolved in phosphate buffer to prepare substrate buffers. When enzyme activity is determined the substrate buffers are used after the addition of sample, dehydrogenase and $NADH_2$ thereto. It is operationally preferable to add previously nonion surfactant to the substrate buffers. The amount of nonion surfactant added to substrate buffer depends more or less on the kind of surfactant used and is generally above several percents (W/V), preferably 5 – 10% (W/V).

According to the method of this invention, serum lipemic turbidity or substances absorbing ultraviolet rays in GOT or GPT-containing samples have hardly any effect on the determination of GOT or GPT activity and the enzyme reaction proceeds over the relatively long time, e.g. from a half to one hour, while the reduction in ultraviolet absorbance of $NADH_2$ is retained linear. Therefore, according to the method, the determination of enzyme activity can be achieved by only one determination of absorbance of $NADH_2$ and then many samples can be readily treated.

The following examples illustrate this invention but are not intended to limit this invention.

EXAMPLE 1

Determination of GOT activity 13.97 g of dipotassium phosphate, 2.69 g of potassium phosphate, 13.3 g of L-aspartic acid, 0.87 g of α-ketoglutaric acid, 0.1 mg of pyridoxal-5'-phosphate, 80 g of Triton X-100 (nonion surfactant available from Rohm and Haas Co.) and 1 g of sodium azide were dissolved in 900 ml of water and the solution was adjusted with sodium hydroxide solution to pH 7.4. To the solution water sufficient to make the total volume 1 liter was added and the obtained solution was used as substrate buffer.

44 units of malic acid dehydrogenase and 13 mg of the reduced type-coenzyme $NADH_2$ were dissolved in 100 ml of the substrate buffer and the resulting solution was used as the enzyme reaction solution. 3 ml of the enzyme reaction solution was added to a test tube in which 0.02 ml of sample solution had previously been charged and the test tube was left standing for precisely one hour at 37° C.

Immediately after the one hour, absorbance at 340 μ ($E_T$) per layer length 10 mm was determined by using water as control. Then, in place of the sample solution, 0.02 ml of water was used in the same manner as the sample solution to determine absorbance at 340 mμ ($E_B$). Thus, absorbance difference $E_B - E_T$ has linear relation with the enzyme activity value of sample solution. FIG. 1 indicates comparison of the above results with results obtained by using the same sample solution as the above sample solution according to the Karmen method. Incidentally, the use of Nikkol CO-60TX (Nonion surfactant available from Nihon Surfactant Kogyo Kabushiki Kaisha) (50 g) in place of Triton X-100 (80 G) gave equally good results having linear relation.

EXAMPLE 2

Determination of GPT activity

The procedure described in Example 1 was repeated except that 8.91 g of DL-alanine was substituted for L-aspartic acid to prepare substrate buffer. To 100 ml of the substrate buffer 22 units of lactic acid dehydrogenase and 13 mg of $NADH_2$ were added to prepare the enzyme reaction solution.

Figure 2:
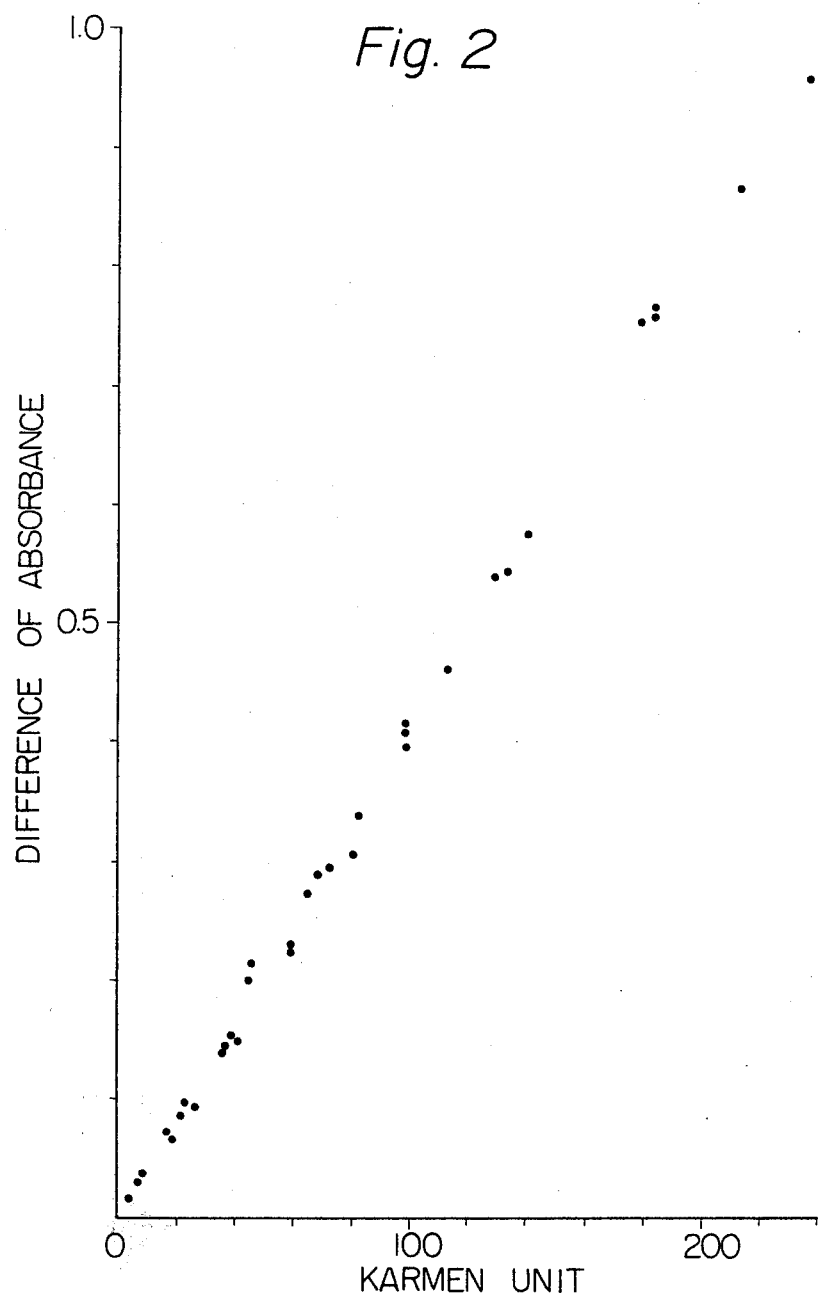

Hereinafter the procedure described in Example 1 was repeated to give the results as indicated in FIG. 2.

What we claim are:

1. In the Karmen method, comprising coupling GOT or GPT with dehydrogenase which reacts with substrates of GOT or GPT are determining GOT or GPT activity by determining the reduction in absorbance in ultraviolet wave length of $NADH_2$ which is coenzyme of the dehydrogenase, the improvement comprising using a GOT or GPT-containing serum sample of about 0.04 to 0.01 ml and adding a nonion surfactant to the reaction system, said surfactant being one which does not inhibit the intended enzyme activity and does not absorb ultraviolet.

2. The improved method according to claim 1 wherein the nonion surfactant is polyoxyethylene alkyl ester, polyoxyethylene sorbitan alkyl ester, isooctylphenyl polyethoxyalcohol or polyoxyethylene castor oil.

3. The improved method according to claim 1 wherein the nonion surfactant is isooctylphenyl polyethoxyalcohol or polyoxyethylene castor oil.

4. The improved method according to claim 1 wherein the amount of nonion surfactant to be added is 5 – 10% (WV) of the substrate buffer solution.

* * * * *

UNITED STATES PATENT AND TRADEMARK OFFICE
CERTIFICATE OF CORRECTION

PATENT NO. : 4,017,365
DATED : April 12, 1977
INVENTOR(S) : NAKAYAMA et al

It is certified that error appears in the above-identified patent and that said Letters Patent are hereby corrected as shown below:

Column 3, line 1, "340 µ" should read --340 mµ--

" " line 15, "(80 G)" should read --(80 g)--

Column 4, line 6, "are" should read --and--

" " line 26, "(WV)" should read --(W/V)--

Signed and Sealed this

Sixth Day of September 1977

[SEAL]

Attest:

RUTH C. MASON
*Attesting Officer*

LUTRELLE F. PARKER
*Acting Commissioner of Patents and Trademarks*